United States Patent
Inci

(10) Patent No.: US 9,968,707 B2
(45) Date of Patent: May 15, 2018

(54) PROCESS FOR BONE TISSUE DECELLULARIZATION

(71) Applicant: Ilyas Inci, Bursa (TR)

(72) Inventor: Ilyas Inci, Bursa (TR)

(\*) Notice: Subject to any disclaimer, the term of this patent is extended or adjusted under 35 U.S.C. 154(b) by 0 days. days.

(21) Appl. No.: 15/156,638

(22) Filed: May 17, 2016

(65) Prior Publication Data

US 2017/0021059 A1 Jan. 26, 2017

(30) Foreign Application Priority Data

May 22, 2015 (EP) .................................... 15169048

(51) Int. Cl.
*A61L 27/36* (2006.01)

(52) U.S. Cl.
CPC ....... *A61L 27/3687* (2013.01); *A61L 27/3608* (2013.01); *C12Y 301/21001* (2013.01); *C12Y 301/27005* (2013.01); *A61L 2430/02* (2013.01); *A61L 2430/40* (2013.01)

(58) Field of Classification Search
CPC .................................................. A61L 27/3687
See application file for complete search history.

(56) References Cited

U.S. PATENT DOCUMENTS

| | | | |
|---|---|---|---|
| 5,797,871 A | 8/1998 | Wolfinbarger, Jr. | |
| 2013/0337560 A1 | 12/2013 | Ross et al. | |

FOREIGN PATENT DOCUMENTS

WO WO-2013188525 A1 \* 12/2013 ........... C12N 5/0654

OTHER PUBLICATIONS

European Search Report dated Nov. 10, 2015 for European patent application No. 15169048.4.
Applicant's reply dated Oct. 6, 2016 to the European Search Report issued for European patent application No. 15169048.4.
Office Action dated Jan. 24, 2017 for European patent application No. 15169048.4.
Applicant's reply dated Oct. 25, 2017 for European patent application No. 15169048.4.
Annex 1 to Applicant's reply dated Oct. 25, 2017 for European patent application No. 15169048.4.
Gilbert Thomas et al "Decellularization of tissues and organs" Biomaterials, Elsevier Science Publisher, BV Barking, GB, vol. 27 No. 19, Jul. 1, 2006.

\* cited by examiner

*Primary Examiner* — Rosanne Kosson

(57) ABSTRACT

A process for preparing decellularized isolated bone tissue samples, comprises the steps of a) providing an isolated bone tissue sample, b) treating said sample by immersions in: a solution comprising at least one chelating agent, a solution comprising at least one anionic detergent, a solution comprising at least one non-ionic detergent, a solution comprising at least one enzyme, a solution comprising at least one antibiotic. Decellularized bone tissue samples as obtainable by a process according to the invention can be used as grafts.

18 Claims, No Drawings

PROCESS FOR BONE TISSUE DECELLULARIZATION

RELATED APPLICATION

This application claims priority to European Patent Application EP 15169048.4, filed May 22, 2015, the contents of which are hereby incorporated by reference as if set forth in their entirety.

FIELD OF THE INVENTION

The present invention relates to a process for the preparation of decellularized bone tissue samples, which can be used as grafts.

BACKGROUND OF THE INVENTION

There is a high demand for functional bone grafts in the United States, as well as in other countries worldwide. More than half a million patients receive bone defect treatments in the United States per year and it costs more than $2.5 billion. This situation is expected to double by 2020 in the United States and in other countries due to many factors, including the growing needs of the increasing populations and increased life expectancy.

Tissue engineering has become an exciting and multidisciplinary field aiming to develop tissues and organs to replace or regenerate defective tissues for almost three decades. Cells, scaffolds and growth-stimulating signals are basic and essential components of the tissue engineering to develop engineered tissues.

Many synthetic materials have been used in the aim of producing scaffolds including polystyrene, poly-l-lactic acid (PLLA), polyglycolic acid (PGA) and poly-dl-lactic-coglycolic acid (PLGA). These materials have shown much success as they can be fabricated with a designed architecture. In addition, their degradation properties can be controlled by changing the polymer concentrations however they have drawbacks including the risk of rejection due to reduced bioactivity.

Another approach to produce scaffold biomaterials is the use of biological materials. Biological polymers such as collagen, proteoglycans, alginate and chitosan have been used in the production of scaffolds for tissue engineering. Unlike synthetic polymer-based scaffolds, natural polymers are biologically active and have properties to promote cell adhesion and growth. In addition, they are also biodegradable and therefore host cells have enough time to produce their own extracellular matrix and replace the degraded scaffold.

However, it is still a challenge to produce scaffolds from biological materials with homogeneous and reproducible structures. Furthermore, the scaffolds which are produced by using biological materials generally have poor mechanical properties and therefore their poor mechanical properties limit their use in, for example, load bearing orthopedic applications.

Transplantation is another approach to provide substitute tissues and organs for defective tissues and organs. However, transplants have serious drawbacks due to problems with providing enough tissue for all of the patients who require them and there are risks of rejection by the patient's immune system. There is also possibility of introducing infection or disease from the donor to the patient. In addition, immune-suppressor drugs should be used after transplantation to prevent organ rejections which make the patients susceptible to many pathogens.

A promising approach to produce functional substitute organs and tissues has emerged in recent years. Decellularization of allogeneic or xenogeneic donor organs such as heart, liver and lung, provides acellular biologic scaffold materials which retain their natural three-dimensional structures. This approach provides the opportunity for direct vascular connection of donor organ to vascular system of the patient.

Particularly difficult is the decellularization of bone tissue. The term "bone tissue" refers specifically to the mineral matrix that form the rigid sections of the organ "bone". There are two types of bone tissue: cortical bone and cancellous bone. Cortical bone is compact, while cancellous bone has a trabecular and spongy structure. The tissues are biologically identical; the difference is in how the microstructure is arranged.

Unlike soft tissue and organs, in view of the structure and the mineralization of the bone tissue, it is a difficult procedure to remove all cells (i.e. decellularize) from bone tissue. In fact, bone cells (osteoblasts, osteocytes and osteoclasts) are embedded in very tightly packed units which are called lacunae; therefore, it is very difficult to perform a complete decellularization of the bone tissue.

US2013/0337560 disclose a method of decellularization of native bone, for example a bone having cortical bone, cancellous bone, a central (medullary)cavity, and cells. In order to decellularize that native bone, one or more apertures are introduced from the exterior of the bone into the central cavity. One or more disruption media are perfused into the central cavity of the bone under condition that provide for decellularization of bone. The medium having cells and/or cellular debris can than flow out of the native arterial and/or venous structures in the bone. However, there is the possibility of remaining cellular components after application of disruption media through holes to larger portions of the bone. Therefore, also in view of the particular microstructure of the bone tissue, the decellularization of bone tissue results very difficult.

Furthermore, the selection of the disruption media to be used can be difficult. In fact, the use of one or more agents and the type of agents used may provide different final decellularization results.

SUMMARY OF THE INVENTION

The aim of the present invention is to solve the problems of the prior art providing a process that allows to decellularize bone tissue easily, effectively and completely.

Another aim of the present invention is to provide bone tissue that is completely decellularized.

Still another aim of the present invention is to provide a completely decellularized bone tissue for the use as graft.

These aims are achieved by the present invention, which relates to a process for preparing a decellularized bone tissue sample comprising the steps of:
  a. providing an isolated bone tissue sample,
  b. treating said sample with:
    i. a solution comprising at least one chelating agent,
    ii. a solution comprising at least one anionic detergent,
    iii. a solution comprising at least one non-ionic detergent,
    iv. a solution comprising at least one enzyme,
    v. a solution comprising at least one antibiotic,
wherein steps b.i. to b.v. are carried out by immersion of said sample in said solutions.

It was surprisingly found that the sequential use of several different agents, can provide better results of decellularization of the bone tissue. In particular, the immersion of the bone tissue sample to be decellularized into several solutions, each one at least comprising a different agent, can easily and effectively provide the complete decellularization of the bone tissue sample.

Another object of the present invention is a decellularized isolated bone tissue sample obtained by a process according to the invention.

A further object of the present invention is a decellularized isolated bone tissue sample obtained by a process according to the invention for the use as graft.

The present invention, as will be explained in greater detail here below, provides a process for producing decellularized bone tissue samples, wherein several different decellularizing agents are applied to remove cellular components. The present invention, in particular, relates to a process wherein an isolated bone tissue sample is treated with at least one chelating agent, at least one anionic detergent, at least one non-ionic detergent, at least one enzyme and at least one antibiotic.

In particular, an isolated bone tissue sample is decellularized by means of several solutions, each containing at least one decellularizing agent.

The use of all this specifically selected agents, was found to be particularly effective and useful to obtain the removal of the cellular material from the sample, without affecting the three dimensional interstitial structure, i.e. the three dimensional structure of the extracellular matrix of the bone sample.

A decellularized bone tissue sample, obtained by means of the process according to the invention, may be used as biologic scaffold for tissue engineering; e.g. it can be used as a graft, for example an allograft or a xenograft.

DETAILED DESCRIPTION

The present invention relates to a process for preparing decellularized isolated bone tissue sample; an isolated bone tissue sample is decellularized by immersion into several different solutions, each containing at least one decellularizing agent.

As used herein, the term "decellularizing agent(s)" refers to any physical, chemical and biological compound or class of compounds, that are suitable to provide cell removal from a tissue, e.g. bone tissue, without altering or negatively affecting the extracellular matrix composition and structure.

Accordingly, the present invention relates to a process for preparing a decellularized isolated bone tissue sample comprising the steps of:
a. providing an isolated bone tissue sample,
b. treating said sample with:
  i. a solution comprising at least one chelating agent,
  ii. a solution comprising at least one anionic detergent,
  iii. a solution comprising at least one non-ionic detergent,
  iv. a solution comprising at least one enzyme,
  v. a solution comprising at least one antibiotic,
wherein steps b.i. to b.v. are carried out by immersion of said sample in said solutions.

Preferably, the process provides for a washing step after each of the above listed steps.

As stated above, all steps b.i. to b.v. are carried out by immersing the isolated bone tissue sample to be treated into the above mentioned solutions. Preferably, the above mentioned steps of the decellularization process are performed by shaking the solutions wherein the bone tissue samples are immersed.

In a particularly preferred embodiment of the present invention, solution of step b.i. is a hypotonic solution, i.e. a hypotonic solution comprising at least one chelating agent.

In a preferred embodiment, a process according to the invention further comprises a step of treating said isolated bone tissue sample with a isotonic solution comprising at least a chelating agent, before performing step b.i. In a particular embodiment, this additional step is performed by immersion of the bone tissue sample in said isotonic solution.

As used herein, the term "isolated bone tissue sample" and "bone tissue sample" refer to isolated samples of bone tissue, for example compact bone or cancellous bone, which have been obtained (i.e. removed) from a human or animal source.

As used herein, the term "decellularized bone tissue sample" and "decellularized isolated bone tissue sample" refer to isolated samples of bone tissue, as defined above, wherein the whole cellular has been removed, leaving intact the three dimensional interstitial structure, e.g. the extracellular matrix structure.

In a preferred embodiment, bone tissue samples are harvested from mammals, such as primates, dogs, cats, mice, rats, cows, horses, pigs, goats and sheep.

In a preferred embodiment, isolated bone tissue samples according to the present invention are provided in the form of slices, the thickness of said slices being in the range of 5 mm to 20 mm, preferably of 17.5 mm, more preferably of 15 mm. In a preferred embodiment, the width of said slices are in the range of 5 mm to 20 mm, preferably of 16 mm. In a preferred embodiment, the length of said slices is in the range of 10 mm to 100 mm, preferably 30 mm. Said samples, i.e. said slices, may be of various shapes. For example, said samples, i.e. said slices, may be of cylindrical or prismatic shape.

For example, an isolated bone tissue sample may have a cylindrical shape, with a diameter in the range of 0.5 cm to 2 cm, preferably of 1.75 cm, and a thickness in the range of 5 mm to 20 mm, preferably of 17.5 mm. Another exemplary shape of an isolated bone tissue sample according to the present invention is a rectangular prism, having height in the range of 5 mm to 20 mm, preferably of 15 mm. In a preferred embodiment, the width of said rectangular prism is in the range of 5 mm to 20 mm, preferably 16 mm. In a preferred embodiment, the length of rectangular prism is in the range of 10 mm to 100 mm, preferably 30 mm.

It has been surprisingly found that such small size of the samples allows an easier diffusion of decellularization agents inside of the bone tissue during immersion, thus allowing the complete removal of the cellular components. In fact, the small size of the samples provides for an extended surface area for decellularizing agents to reach into the bone tissue so decellularizing agents can remove cellular components easily.

After the decellularization of the samples, a decellularized bone tissue sample is obtained, having preferably the same shape and the same dimension of the bone tissue sample before the treatment.

For example, a decellularized bone tissue sample according to the invention, can have a thickness in the range of 5 mm to 20 mm, preferably of 17.5 mm, more preferably of 15 mm.

After harvesting, the bone tissue samples are preferably washed, e.g. washed with water. In particular, when, for example, samples of cancellous bone are harvested, it is preferably to carry out a washing step, e.g. with water, in order to remove the bone marrow in the pores.

In a preferred embodiment, a process according to the invention, further comprises a step of treating said isolated bone tissue sample with an isotonic solution comprising at least a chelating agent before performing step b.i. For example, an isolated bone tissue sample after harvesting, may be washed with water, and additionally washed with an isotonic solution comprising at least a chelating agent, e.g. EDTA (Ethylenediaminetetraacetic acid). An exemplary solution of said isotonic solution is a solution comprising EDTA and PBS (Phosphate Buffer Saline) buffer.

In a preferred embodiment of the present invention, at least a chelating agent is selected from EDTA (Ethylenediaminetetraacetic acid) and EGTA (ethylene glycol tetraacetic acid) and mixtures thereof. More in detail, in preferred embodiments said chelating agent is used in a concentration in the range of 0.05 g/100 ml of solution to 0.5 g/100 ml of solution: preferably, the concentration of said at least one chelating agent is of 0.1 g/100 ml of solution. Said concentration values can be applied both to the above discussed isotonic solution and the solution of step b.i. of the process of the invention. As already mentioned, in a particularly preferred embodiment of the present invention, solution of step b.i. is a hypotonic solution, i.e. a hypotonic solution comprising at least one chelating agent.

A possible explanation of the effectiveness of the above mentioned solutions comprising at least a chelating agent in the process of decellularization of a bone tissue sample can be that chelating agents bind to the divalent cations such as $Ca^{2+}$ and $Mg^{2+}$ which has functions in cell adhesion therefore these agents can catalyze the removal of the cellular material from the tissue.

Suitable anionic detergents according to the invention are, for example, SDS (Sodium dodecyl sulfate), Sodium deoxycholate, ammonium lauryl sulfate, sodium 2-ethylhexyl sulfate, sodium decane sulfonate, sodium heptane sulfonate, sodium octane sulfonate, sodium hexane sulfonate, sodium propane sulfonate, sodium pentane sulfonate, sodium butane sulfonate, sodium nonane sulfonate, Triton X-200®, Triton XQS-20®, Triton QS-15®, Triton QS-44®, N-laurylsarcosine sodium salt, dicyclohexyl sulfosuccinate, docusate sodium salt, dihexadecyl phosphate and dihexyl sulfosuccinate, and mixtures thereof. The preferred anionic detergent is SDS. In a preferred embodiment, said anionic detergent is used in a concentration in the range of 0.1 g/100 ml of solution to 1 g/100 ml of solution, preferably 0.5 g/100 ml of solution.

Suitable non-ionic detergent according to the invention are, for example, Triton X-100® (Polyethylene glycol tert-octylphenyl ether), Tween 20® (Polyethylene glycol sorbitan monolaurate), Tween 80® (Polyethylene glycol sorbitan monooleate), Igepal® CA 630 (Octylphenoxy poly(ethyleneoxy)ethanol) and N-octyl-β-D glucopyranoside, Brij 35®, Brij 56®, Brij 72®, Brij 76®, Brij 92V®, Brij 97®, Brij 58P®, digitonin, digitoxigenin, Genapol C-100®, N,N-dimethyl dodecylamine N-oxide, Nonidet P40®, octaethylene glycol monododecyl ether, octaethylene glycol monooctadecyl ether, saponin, Span 20®, Span 60®, Span 65®, Span 80®, Span 85® and Tergitol®, and mixtures thereof. The preferred non-ionic detergent is Triton X-100® (Polyethylene glycol tert-octylphenyl ether). In a preferred embodiment, said non-ionic detergent is used in a concentration in the range of 0.1% v/v to 5% v/v, preferably 1% v/v on the total volume of the solution.

It was found that non-ionic and anionic detergents are useful to carry out the decellularization of a bone tissue sample. In particular the use of both of them, sequentially, or mixtured in the same treating solution, provides an effective disruption of lipid-lipid, lipid-protein and protein-protein interactions of the treated tissue, thus providing disruption of the cellular material from the sample of without negatively affect the three-dimensional structure of bone tissue, i.e. the extracellular matrix structure, and its composition.

In a preferred embodiment, enzymes suitable to be used in the present process are those selected from nucleases; preferably those selected from DNases, RNases and a mixtures thereof. In a preferred embodiment, other suitable enzymes according to the invention are trypsin, collagenase, lipase, phosphase and dispase, or mixtures thereof. Suitable DNase according to the invention are, for example, DNase I, DNase II alpha and DNase II beta; exemplary RNase suitable for the use according to the present invention are, for example, RNase A, RNase IIIA, RNase IIIB, RNase H, RNase L and RNase P. In a more preferred embodiment, the selected DNase is DNase I; and/or the selected RNase is RNase A.

In a more preferred embodiment, a solution according to step b.iv. comprises at least a endonuclease, preferably at least a DNase and/or a RNase; more preferably, it comprises at least DNase I and/or RNase A. For example, a possible solution according to step b.iv. comprises at least a DNase in a concentration in the range of 5 units/ml to 500 units/ml, preferably 50 units/ml, and/or at least one RNase in a concentration in the range of 0.5 units/ml to 50 units/ml, preferably 1 unit/ml. In a most preferred embodiment, the solution according to step b.iv. comprises both a DNase and a RNase, preferably DNase I and RNase A.

This step was found to be particularly effective, when carried out after the treatment of the sample with a solution comprising one or more anionic and/or one or more non-ionic detergent. By using nucleases, nuclear components of tissue are removed from the tissue.

In a preferred embodiment, steps b.i. to b.iv. are performed according to the sequence: b.i., b.ii., b.iii., b.iv. In other embodiments, said steps b.i. to b.iv. may be performed in any procedural sequence, changing the order of performing the different steps. For example, in a preferred embodiment, non-ionic detergents can be used before anionic detergents. In a preferred embodiment, antibiotics can be used during and/or after each step b.i. to b.iv.; in this particular embodiment the use of the antibiotics during and/or after each step allows to prevent contamination of the samples.

In embodiments of the present invention, the process of the invention can further comprise one or more steps, wherein the bone tissue sample is treated with one or more decellularizing agents which can be the same as, or other than, those used in already performed steps. For example, a process according to the invention can comprise a further step wherein the bone tissue sample is treated with a solution comprising at least one enzyme, according to step b.iv. In other words, for example, a process according to the invention can comprise a step of treatment of the bone tissue sample with a first solution comprising a DNase and/or a RNase, and a further step wherein the bone tissue sample is treated with a second solution comprising a different enzyme, for example, an enzyme selected from trypsin, collagenase, lipase, phosphase and dispase, or mixtures thereof.

The same apply for all the decellularizing agents herein discussed.

As stated above, a preferred steps b.i. to b.iv. are performed according to the sequence: b.i., b.ii., b.iii., b.iv., and subsequently b.v. it has been surprisingly found that performing these steps in this sequence is particularly advantageous. A possible explanation, can be that chelating agents which bind to the divalent cations such as $Ca^{2+}$ and $Mg^{2+}$, provides for detachment and removal of the cellular material from the tissue is obtained. Thus, after this first removal of the cells by using chelating agents, the use of anionic detergents and non-ionic detergents was found to be particularly effective in removing remaining protein and lipid residuals. A possible explanation can be that non-ionic detergents have disruptive effect on lipid-lipid and lipid-protein interactions; however non-ionic detergents have no disruptive effect on protein-protein interactions so protein-protein bounds remain intact with their three dimensional and functional conformations. Anionic detergents are also used, which are effective for disrupting both cytoplasmic and nuclear cellular membranes; in addition they tend to denature proteins by disrupting protein-protein interactions. After removal of cells and then removal of protein and lipid residuals, enzymes, for example, DNase and RNase allow the removal of DNA and RNA from the sample. In this way, a hierarchy in removal of compartments is followed. First, biggest parts, cells are removed and then protein and lipid residuals are removed. In last stage, the smallest compartments which are DNA and RNA removed. In this way, the best efficacy of each decellularizing agent is obtained. According to step b.v. of the process of the present invention, suitable antibiotics are those selected from penicillin, streptomycin, amphotericin B, gentamicin, kanamycin, neomycin, ampicillin, chloramphenicol, ciprofloxacin, puromycin and tetracycline, and mixtures thereof. In a preferred embodiment, a solution according to step b.v. comprises at least penicillin and/or streptomycin. For example, penicillin can be used in a concentration in the range of 10 units/ml to 1000 units/ml, preferably 100 units/ml; and/or streptomycin can be used in a concentration in the range of 10 µg/ml to 1000 µg/ml, preferably 100 mg/ml. in a preferred embodiment, a solution according to step b.v. comprises at least both penicillin and streptomycin, wherein these two antibiotics are present, preferably, in a concentration in the range of, respectively, 10 units/ml to 1000 units/ml (penicillin) and 10 µg/ml to 1000 µg/ml (streptomycin).

As already mentioned, according to a preferred embodiment of the process which the present invention relates to, the bone tissue sample is washed, preferably after each step, preferably with buffer solution, to remove used agents.

In a preferred embodiment, a process according to the present invention further comprises a step of freeze drying. In this case, a decellularized bone tissue sample obtained with a process comprising steps a. and b.i.-b.v., can be freeze dried by using, for example, a freeze-dryer, in order to remove residual water or buffer.

Freeze-dried decellularized bone tissue samples may be cut into desired size and shapes, suitable to be used as grafts.

In a preferred embodiment, a process according to the present invention further comprises a step of sterilization. In a preferred embodiment, said sterilization is performed by means of ethylene oxide gas. Another suitable sterilization method, according to the invention, is gamma ray sterilization. In a particularly preferred embodiment, said sterilization step, for example with ethylene oxide gas, is performed after the free-drying of the bone sample and its cutting. When the sterilization step with ethylene oxide gas is carried out, the obtained decellularized bone tissue samples, i.e. bone grafts, are preferably ventilated under sterile conditions after sterilization, to remove remaining toxic ethylene oxide gas which might be in the pores of the decellularized bone tissue samples.

In a preferred exemplary embodiment, a process preparing a decellularized isolated bone tissue sample according to the present invention, for example, comprises the steps of:
 a. providing an isolated bone tissue sample,
 b. treating said sample with:
  i. a hypotonic solution comprising at least EDTA (Ethylenediaminetetraacetic acid),
  ii. a solution comprising at least SDS (Sodium dodecyl sulfate),
  iii. a solution comprising at least Triton X-100® (Polyethylene glycol tert-octylphenyl ether),
  iv. a solution comprising at least one DNase and/or at least one RNase,
  v. a solution comprising at least penicillin and/or streptomycin,
wherein steps b.i. to b.v. are carried out by immersion of said sample in said solutions.

In another preferred exemplary embodiment, a process preparing a decellularized isolated bone tissue sample according to the present invention, for example, comprises the steps of:
 a. providing an isolated bone tissue sample,
  i. washing said sample with water,
  ii. washing said sample with a isotonic solution comprising at least EDTA (Ethylenediaminetetraacetic acid),
 b. treating said sample with:
  i. a hypotonic solution comprising at least EDTA (Ethylenediaminetetraacetic acid),
  ii. a solution comprising at least SDS (Sodium dodecyl sulfate),
  iii. a solution comprising at least Triton X-100® (Polyethylene glycol tert-octylphenyl ether),
  iv. a solution comprising at least one DNase and/or at least one RNase,
  v. a solution comprising at least penicillin and/or streptomycin,
 c. freeze-drying the obtained treated sample,
 d. sterilizing the obtained freeze-dried sample with ethylene oxide gas.
wherein steps a.i., a.ii. and b.i. to b.v. are carried out by immersion of said sample in said solutions.

As mentioned above, another object of the present invention is a decellularized isolated bone tissue sample obtained by a process according to the invention.

The present process presents several advantages over the processes known in the art. For example, in the present process, bone is advantageously cut in very small dimensions when compared with other protocols. The small size of samples give advantage to present process since it would be easier for diffusion of decellularization agents inside of the bone tissue during immersion, thus allowing the complete removal of the cellular components. In fact, in view of the fact that bone tissue is cut into thin bone samples and said bone samples are immersed into solutions of decellularizing agents, there is an extension of surface area for decellularizing agents to reach into the bone tissue so decellularizing agents can remove cellular components easily. Another advantage of the present process is that a hierarchy in removal of compartments is followed. In fact, biggest parts, cells are removed first, and then protein and lipid residuals are removed. In last stage, the smallest compartments which are DNA and RNA removed. In this way, the best efficacy of each decellularizing agent is obtained.

A decellularized isolated bone tissue sample obtained by a process according to the invention is suitable for the use as graft. In particular, is suitable to be used as an allograft or a xenograft. An allograft, is a tissue graft from a donor of the same species as the recipient but not genetically identical, while, on the contrary, a xenograft is a tissue graft or organ transplant from a donor of a different species from the recipient.

The present invention has several advantages over the prior art. For example, the present process is suitable to decellularize bone tissue harvested in form of "thin" slices, i.e. having reduced thickness and dimension, providing an effective removal of the cellular content from the tissue, without damaging or negatively affecting the three-dimensional structure of the extracellular matrix. This is particularly true in view of the fact that the isolated bone sample are treated by immersion, and preferably shaking, into solutions of selected decellularizing agents; this particular approach allows to decellularize the tissue effectively as well as gently, i.e. completely removing cells without damaging the structure of the matrix. Additionally, by immersion into solution of decellularizing agents, there is an extension of surface area of the bone tissue sample exposed to decellularizing agents; in this view, decellularizing agents can reach all the cellular material to be removed that is present in the sample.

The present invention will be hereinafter further illustrated by the following non-limiting example.

EXAMPLES

1) Isolation of Bone Tissue Samples

The subchondral zone (the area under the cartilage tissue) of cancellous bone (porous bone) of between 2 weeks-4 month old calves is cut using a milling machine with a cylindrical shape of 1.75 cm in diameter and variable lengths or cancellous bone can be cut 1.5 cm×1.6 cm in size to achieve the same volumetric space and into a rectangular prism having different lengths.

2) Washing with Water and Isotonic Solution Comprising EDTA

The cut bone is washed under high velocity water to remove the bone marrow in the pores, 0.1 g of EDTA (Ethylene diamine tetraacetic acid) is dissolved in 100 ml Phosphate Buffered Saline (PBS) by using a magnetic fish in a glass beaker on a magnetic stirrer. Bone pieces are put into prepared PBS-EDTA solution at room temperature and washed for 1 hour by using an orbital shaker with a shaking speed without making any damage to the bone graft.

3) Solution Comprising at Least One Chelating Agent

Hypotonic buffer solution is prepared but before preparing the hypotonic buffer, Tris buffer solution should be prepared. For preparing Tris buffer (10 millimolar), 1.2 g of Tris is dissolved in 650 milliliters distilled water. Then 16.5 milliliters of the commercially available 37% concentration of hydrochloric acid is added into 83.5 milliliters of distilled water to prepare 2 molar hydrochloric acid solution to adjust pH of Tris buffer solution. After that, 2 molar hydrochloric acid is added into Tris buffer and the pH of solution adjusted to pH 7.5 with the aid of a pH meter. After pH-adjustment, the volume of Tris buffer solution is made up to 1000 milliliters. Then 0.1 grams of EDTA is added into 100 ml of Tris buffer solution by using a magnetic stirrer to prepare hypotonic buffer solution. Bone tissue samples are washed by using the orbital shaker overnight at 4° C. in the solution which is prepared by using Tris and EDTA. Subsequently, samples are washed for 1 hour in PBS by using an orbital shaker with shaking speed to prevent damage to the samples.

4) Solution Comprising at Least One Anionic Detergent

The anionic detergent solution is prepared. For this purpose, 0.5 grams of SDS (sodium dodecyl sulfate) is dissolved 100 ml of Tris buffer solution in a glass beaker by mixing with a magnetic stirrer. Samples are put into prepared detergent solution and washed by using an orbital shaker at room temperature for 24 hours with shaking speed to prevent damage to the samples.

Subsequently, bone tissue samples are washed 7 times in PBS for 1 hour by using an orbital shaker and filled with fresh PBS after each wash. These repeated washing steps are necessary to prevent formation of bubbles resulting from SDS.

5) Solution Comprising at Least One Non-Ionic Detergent

Non-ionic detergent solution containing 1% Triton X-100 is prepared. For this purpose, 1 ml of Triton X-100 is dissolved in 100 milliliters of Tris buffer solution by using magnetic stirrer. Samples are put into prepared detergent solution and washed by using an orbital shaker at 25° C. for 24 hours with shaking speed to prevent damage to the bone tissue samples. Subsequently, samples are washed 7 times in PBS for 1 hour by using an orbital shaker and filled with fresh PBS after each wash. These repeated washing steps are necessary to prevent formation of bubbles resulting from Triton X-100.

6) Solution Comprising at Least One Enzyme

Subsequently the enzyme solution is prepared. Before preparing the enzyme solution, preparation of salt (NaCl) solution is required. 0.88 g NaCl is dissolved in 100 milliliters of distilled water. 1.25 milligrams of DNase I (stock: 2000 units/mg) is dissolved in 5 ml of saline solution by using a magnetic stirrer. 1 mg of RNase A (stock: 70 units/mg) is dissolved in 70 ml distilled water by using a magnetic stirrer to prepare RNase solution. An activation solution should be prepared for DNase enzyme. For this purpose, 0.12 g of Tris, 0.024 g of magnesium chloride and 0.006 g of calcium chloride are dissolved in 65 ml distilled water. Then pH of the activation solution is adjusted to pH 7.5 by using 2 molar hydrochloric acid and a pH meter. After pH adjustment, the volume of activation solution is adjusted up to 100 milliliters. 5 ml of prepared DNase solution and 500 microliters of prepared RNase solution are added into 44 ml of activation solution. Finally, 500 microliters of activation solution is added for completion of volume to 50 ml and dissolved by using a magnetic stirrer. Bone tissue samples are put into prepared enzyme solution and placed into the oven arranged at 37° C. for 6 hours and washed by using an orbital shaker for 24 hours with shaking speed to prevent damage to the samples. Subsequently, samples are washed 7 times in PBS for 1 hour by using an orbital shaker and filled with fresh PBS after each wash.

7) Solution Comprising at Least One Antibiotic

Antibiotics solution is prepared. An antibiotics solution is prepared which contains 100 units/ml of penicillin and 100 micrograms/ml of streptomycin. 1 ml of commercially available antibiotics solution which contains 10000 units/ml penicillin and 10 mg/ml of streptomycin is added into 99 milliliters of Tris buffer solution to prepare antibiotic solution by using magnetic stirrer. Bone tissue samples are put into prepared antibiotics solution and washed at 4° C. for 48 hours by using an orbital shaker with shaking speed to prevent damage to the samples. Subsequently, samples are washed 7 times in PBS for 1 hour by using an orbital shaker and filled with fresh PBS after each wash.

8) Freeze-Drying and Sterilization

The washed bone tissue samples are freeze-dried for 48 hours by using freeze-dryer to remove water. The freeze-dried samples are cut into the desired size, to prepare bone grafts, and are sterilized by using ethylene oxide gas. Prepared bone grafts should be ventilated thoroughly under sterile conditions to remove remaining toxic ethylene oxide gas which might be in the pores.

The invention claimed is:

1. A process for preparing a decellularized isolated bone tissue sample, comprising the steps of:
   a. providing an isolated bone tissue sample, and
   b. treating said isolated bone tissue sample with:
   i. a solution comprising at least one chelating agent,
   ii. a solution comprising at least one anionic detergent,
   iii. a solution comprising at least one non-ionic detergent,
   iv. a solution comprising at least one enzyme, and
   v. a solution comprising at least one antibiotic,
   wherein said steps b.i. to b.v. are carried out by immersion of said isolated bone tissue sample in said respective solutions, and wherein said step b.i is carried out before said step b.ii, said step b.ii is carried out before said step b.iii, said step b.iii is carried out before said step b.iv, and said step b.iv is carried out before said step b.v.

2. The process according to claim 1, wherein said solution comprising at least one chelating agent is a hypotonic solution.

3. The process according to claim 1, further comprising a step of treating said isolated bone tissue sample with an isotonic solution comprising at least a chelating agent, before said step b.

4. The process according to claim 1, wherein said chelating agent comprises one of EDTA (Ethylenediaminetetraacetic acid), EGTA (ethylene glycol tetraacetic acid) and a mixture thereof.

5. The process according to claim 1, wherein said chelating agent is present in a concentration range of 0.05 g/100 ml of solution to 0.5 g/100 ml of solution.

6. The process according to claim 1, wherein said anionic detergent is selected from the group consisting of SDS (Sodium dodecyl sulfate), Sodium deoxycholate, ammonium lauryl sulfate, sodium 2-ethylhexyl sulfate, sodium decane sulfonate, sodium heptane sulfonate, sodium octane sulfonate, sodium hexane sulfonate, sodium propane sulfonate, sodium pentane sulfonate, sodium butane sulfonate, sodium nonane sulfonate, Triton® X-200, Triton® XQS-20, Triton® QS-15, Triton® QS-44, N-laurylsarcosine sodium salt, dicyclohexyl sulfosuccinate, docusate sodium salt, dihexadecyl phosphate and dihexyl sulfosuccinate, and mixtures thereof.

7. The process according to claim 1, wherein said anionic detergent is present in a concentration range of 0.1 g/100 ml of solution to 1 g/100 ml of solution.

8. The process according to claim 1, wherein said non-ionic detergent is selected from the group consisting of Triton® X-100 (Polyethylene glycol tert-octylphenyl ether), Tween® 20 (Polyethylene glycol sorbitan monolaurate), Tween® 80 (Polyethylene glycol sorbitan monooleate), Igepal® CA 630 (Octylphenoxy poly(ethyleneoxy) ethanol) and N-octyl-p-D glucopyranoside, Brij® 35, Brij® 56, Brij® 72, Brij® 76, Brij® 92V, Brij® 97, Brij® 58P, digitonin, digitoxigenin, Genapol® C-100, N,N-dimethyl dodecylamine N-oxide, Nonidet® P40, octaethylene glycol monododecyl ether, octaethylene glycol monooctadecyl ether, saponin, Span® 20, Span® 60, Span® 65, Span® 80, Span® 85, and Tergitol®, and mixtures thereof.

9. The process according to claim 1, wherein said non-ionic detergent is present in a concentration range of 0.1% to 5% of the total volume of said solution.

10. The process according to claim 1, wherein said enzyme is selected from a DNase, an RNase, and a mixture thereof.

11. The process according to claim 1, wherein said antibiotic is selected from the group consisting of penicillin, streptomycin, amphotericin B, gentamicin, kanamycin, neomycin, ampicillin, chloramphenicol, ciprofloxacin, puromycin and tetracycline and mixtures thereof.

12. The process according to claim 1, wherein said solution comprising at least one antibiotic comprises at least one of penicillin present in a concentration range of 10 units/ml to 1000 units/ml, and streptomycin present in a concentration range of 10 μg/ml to 1000 μg/ml.

13. A decellularized bone tissue sample as obtainable by a process according to claim 1.

14. The decellularized bone tissue sample according to claim 13, wherein said decellularized bone tissue sample has a thickness of 5 mm to 20 mm.

15. The decellularized bone tissue sample according to claim 13, adapted for use as a graft.

16. The decellularized bone tissue sample according to claim 13, wherein said decellularized bone tissue sample has a thickness of about 15 mm to about 17.5 mm.

17. The process according to claim 10, wherein said enzyme is selected from said DNase present in a concentration range of 5 units/ml to 500 units/ml in said solution comprising at least one enzyme, and said RNase present in a concentration range of about 0.5 units/ml to about 50 units/ml in said solution comprising at least one enzyme.

18. The process according to claim 10, wherein said enzyme is selected from said DNase present in a concentration of about 50 units/ml in said solution comprising at least one enzyme, and said RNase present in a concentration of about 1 unit/ml in said solution comprising at least one enzyme.

* * * * *